United States Patent
Kumosani et al.

(10) Patent No.: US 10,226,501 B2
(45) Date of Patent: Mar. 12, 2019

(54) METHOD OF ORALLY ADMINISTERING A DATE FRUIT EXTRACT TO TREAT BREAST CANCER

(71) Applicant: King Abdulaziz University, Jeddah (SA)

(72) Inventors: Taha Abdullah Kumosani, Jeddah (SA); Elie Kamil Barbour, Jeddah (SA); Fazal Khan, Jeddah (SA); Kalamegam Gauthaman, Jeddah (SA); Adel Abuzenadah, Jeddah (SA)

(73) Assignee: King Abdulaziz University, Jeddah (SA)

(*) Notice: Subject to any disclaimer, the term of this patent is extended or adjusted under 35 U.S.C. 154(b) by 0 days.

(21) Appl. No.: 15/622,493

(22) Filed: Jun. 14, 2017

(65) Prior Publication Data

US 2018/0360902 A1   Dec. 20, 2018

(51) Int. Cl.
| | | |
|---|---|---|
| *A61K 36/889* | (2006.01) | |
| *A61K 9/00* | (2006.01) | |
| *A61K 9/08* | (2006.01) | |

(52) U.S. Cl.
CPC .......... *A61K 36/889* (2013.01); *A61K 9/0053* (2013.01); *A61K 9/08* (2013.01); *A61K 2236/15* (2013.01); *A61K 2236/33* (2013.01); *A61K 2236/51* (2013.01); *A61K 2236/53* (2013.01)

(58) Field of Classification Search
None
See application file for complete search history.

(56) References Cited

U.S. PATENT DOCUMENTS

2011/0223191 A1*  9/2011  Mohamed ............... A61K 36/02
424/195.17

FOREIGN PATENT DOCUMENTS

| JP | 2012 240996 | * 12/2012 | |
|---|---|---|---|
| WO | 2010/110639 | 9/2010 | |
| WO | 2013/049519 | 4/2013 | |

OTHER PUBLICATIONS

Eid, N. et al. Impact of Palm Date Consumption on Microbiota Growth and Large Intestinal Health. British J of Nutrition 114(8)1226-1236, Oct. 28, 2015. (Year: 2015).*

Khan, F. et al. Ajwa Date Extract Inhibits Human Breast Adenocarcinoma Cells in vitro by Inducing Apoptosis and Cell Cycle Arrest. PLoS One, 11(7)60-69, Jul. 21, 2016. (Year: 2016).*

Khalid, S. et al. A Review on Chemistry and Pharmacology of Ajwa Date Fruit and Pit. Trends in Food Science & Tech 63:60-69, 2017. (Year: 2017).*

Al-Yahya, M. et al. Ajwa Dates Extract Ameliorates Isoproterenol Induced Cardiomyopathy . . . Phytomedicine 23:1240-48, 2016. Year: (2016).*

Abutaha N. Apoptotic Potential of Ethyl Acetate Fraction of Cochliobolus Spicifer . . . Research J of BioTechnology 10(12)14-21, 2015 . (Year: 2015).*

Al-Sayyed H. et al. The Effect of Date Palm Fruit on the Hormone 17 Beta Estradiol . . . Mediterranean J of Nutrition and Metabolism 7(1)5-10, 2014. (Year: 2014).*

Siahpoosh A. et al. Antioxidant and Hydroxyl Radical Scavenging Activity of *Phoenix dactylifera* L. . . . Iranian J of Pharmaceutical Res 12(Suppl 2) 140, Oct. 2013. (Year: 2013).*

Naskar S. et al. In vitro and in vivo Antioxidant Potential of Hydromethanolic Extract of Phoenix dactylifera Fruits. 2(1)144-157, 2010. (Year: 2010).*

Sultana B. et al. In vitro Synergism of Antimutagenic and Antioxidant Activities of Phoenix datylifera Fruit. Food Science and Biotechnology 23(3)881-887, 2014. (Year: 2014).*

Al-Alawi R. et al. Date Palm Tree Natural Products and Therapeutic Options. Frontiers in Plant Science 8:845 May 2017. (Year: 2017).*

Nael Abutaha, "Apoptotic Potential of Ethyl Acetate Fraction of Cochliobolus spicifer (Pleosporales: Pleosporaceae) isolated from *Phoenix Dactylifera* L. on Human Cancer Cell Lines," Dec. 2015.

Nael Abutaha et al., "Antiproliferative and antibacterial metabolites from endophytes isolated from calotropis procera and Phoenix dactylifera," Research Journal of Biotechnology, vol. 10, No. 10, Oct. 2015.

Bibi R. Yasin et al., "Date (Phoenix dactylifera) Polyphenolics and Other Bioactive Compounds: A Traditional Islamic Remedy's Potential in Prevention of Cell Damage, Cancer Therapeutics and Beyond," International Journal of Molecular Sciences, vol. 16, Dec. 17, 2015, pp. 30075-30090.

Fazal Khan et al., "Ajwa Date (*Phoenix dactylifera* L.) Extract Inhibits Human Breast Adenocarcinoma (MCF7) Cells In Vitro by Inducing Apoptosis and Cell Cycle Arrest," Jul. 21, 2016.

Magaji Abdullahi et al., "Medicinal value of Date palm (*Phoenix dactylifera* L.)," Nov. 2012.

Dalia H.A. Abdelaziz et al., "The protective effect of *Phoenix dactylifera* L. seeds against CCl4-induced hepatotoxicity in rats," Journal of Ethnopharmacology, vol. 155, No. 1, Aug. 8, 2014.

* cited by examiner

*Primary Examiner* — Ralph J Gitomer

(74) *Attorney, Agent, or Firm* — Oblon, McClelland, Maier & Neustadt, L.L.P.

(57) ABSTRACT

A method for treating a cancer in a mammal using an extract of a *Phoenix dactylifera* (i.e. date) fruit flesh is described, along with an extraction method. The extract may be formed into a dried powder and reconstituted into a variety of media for oral administration, intravenous administration, or other routes. The extract may also be administered to prevent the occurrence of cancer or to treat other ailments.

20 Claims, 11 Drawing Sheets

METHOD OF ORALLY ADMINISTERING A DATE FRUIT EXTRACT TO TREAT BREAST CANCER

BACKGROUND OF THE INVENTION

Technical Field

The present invention relates to a method of making an extract from a *Phoenix dactylifera* fruit flesh and using it to treat or prevent a cancer in a mammal.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

There is no presence of any United States or International published or submitted patents that document data related to Ajwa Dates (*Phoenix dactylifera* L.) extracts possessing anti-cancer properties. Below is a list of US and International patents that are related to treatment and prevention of cancer by different fruit extracts. Each patent is incorporated herein by reference in its entirety.

US Patent Publication No. 20070248693, publication date Oct. 25, 2007, describes a nutraceutical composition, extracted from many plants, for treatment of cancer. U.S. Pat. No. 8,034,386, publication date Oct. 11, 2011, discloses an extract of *Agaricus Blazei Murill* that suppresses breast cancer. U.S. Pat. No. 8,569,382, publication date Oct. 29, 2013, discloses an extract and its single or combined compounds of *Phaleria macrocarpa* that have an anti-neoplastic effect. US Patent Publication No. 20150110862, publication date Apr. 23, 2015, describes an extract from sweet gum (*Liquidambar styraciflua* L.) fruit that inhibits multiple targets of the P13K pathway, leading to inhibition of various cancer cells. US Patent Publication No. 20150125560, publication date May 7, 2015, discloses a composition for preventing or treating cancer, containing extracts of *Artocarpus altilis* fruits, leaves, or stems, or active ingredients present in its extracted fractions. U.S. Pat. No. 9,248,156, publication date Feb. 2, 2016 discloses an extract from *Piper cubeba* L. for treatment of cancer. Foreign Patent No. EP 1094813, publication date Sep. 10, 2003, discloses the use of piperine, present in pepper, and its alkaloid derivatives, for treating skin cancer.

In view of the foregoing, one objective of the present invention is to provide a method for treating cancer by administering a therapeutically effective dose of an extract of a *Phoenix dactylifera* fruit flesh. The cancer may be breast cancer or liver cancer, and the extract may be administered orally, including as a dietary supplement.

BRIEF SUMMARY OF THE INVENTION

According to a first aspect, the present disclosure relates to a method for treating a cancer in a mammal comprising administering a therapeutically effective dose of an extract of a *Phoenix dactylifera* fruit flesh to the mammal.

In one embodiment of the method, the cancer is breast cancer or liver cancer.

In one embodiment of the method, the therapeutically effective dose is 0.1 to 5 g of the extract per kg of the mammal per day.

In one embodiment of the method, the extract comprises p-coumaric acid, ferulic acid, sinapinic acid, a β-glucan, a flavonoid, a procyanidin, or a polyphenol.

In one embodiment of the method, the administering is by a mode of oral administration, intravenous administration, topical administration, inhalation spray, rectal administration, topical administration, intradermal administration, transdermal administration, subcutaneous administration, intramuscular administration, intralesional administration, intrapulmonal administration, sublingual administration, or intratumoral administration.

In one embodiment of the method, the therapeutically effective dose is administered orally, and the therapeutically effective dose is 0.1 to 5 g of the extract per kg of the mammal per day.

In one embodiment of the method the cancer is breast cancer, and the method further comprises measuring an activity of at least one enzyme in a serum of the mammal, wherein the activity of at least one enzyme in the serum of the mammal is increased 2%-50% after the administering compared to an activity prior to the administering, and the enzyme is superoxide dismutase, catalase, glutathione reductase, or glutathione peroxidase.

In one embodiment of the method, the cancer is liver cancer, and the method further comprises measuring an activity of at least one enzyme in a serum of the mammal, wherein the activity of at least one enzyme in the serum of the mammal is increased 2%-110% after the administering compared to an activity prior to the administering, and the enzyme is superoxide dismutase, catalase, glutathione reductase, or glutathione peroxidase.

In one embodiment of the method, the cancer is liver cancer, and the method further comprises measuring an expression level of at least one cytokine, wherein after the administering an IL-2 expression level of the cancer is increased 20%-80% relative to an IL-2 expression level of the cancer before the administering, a G-CSF expression level of the cancer is increased 25%-50% relative to a G-CSF expression level of the cancer before the administering, an MIP-1a expression level of the cancer is increased 30%-80% relative to an MIP-1a expression level of the cancer before the administering, or a GM-CSF expression level of the cancer is increased 80%-110% relative to a GM-CSF expression level of the cancer before the administering.

In one embodiment of the method, the extract is made by contacting a *Phoenix dactylifera* fruit flesh with an organic solvent, and the organic solvent is methanol, ethanol, 1-propanol, 2-propanol, 1-butanol, 2-butanol, tert-butyl alcohol, ethyl acetate, acetone, or acetonitrile.

In a further embodiment, where the extract is made by contacting a *Phoenix dactylifera* fruit flesh with an organic solvent, the organic solvent is methanol.

In a further embodiment, where the extract is made by contacting a *Phoenix dactylifera* fruit flesh with an organic solvent, a weight ratio of the *Phoenix dactylifera* fruit flesh to the organic solvent is 1:1.5-1:3.

In a further embodiment, where the extract is made by contacting a *Phoenix dactylifera* fruit flesh with an organic solvent, the contacting is done for 12-96 h at 20-30° C.

In a further embodiment, where the extract is made by contacting a *Phoenix dactylifera* fruit flesh with an organic solvent, the *Phoenix dactylifera* fruit flesh is ground, blended, or cut.

In one embodiment of the method, the extract is administered as a part of a composition, wherein the composition further comprises a food product, a pharmaceutically acceptable excipient, a pharmaceutically acceptable carrier, or an antioxidant.

In a further embodiment, the composition is formed by reconstituting the extract into a liquid or gel, and the extract is in the form of a dried powder before reconstituting.

In a further embodiment, where the extract is administered as a part of a composition comprising a pharmaceutically acceptable carrier, the pharmaceutically acceptable carrier is an isotonic solution.

In a further embodiment, where the extract is administered as a part of a composition comprising a pharmaceutically acceptable antioxidant, the antioxidant is melatonin, astaxanthin, tocotrienol, tocopherol, or lycopene.

According to a second aspect, the present disclosure relates to a method for preventing cancer in a mammal comprising orally administering 0.1 to 5 g of an extract of a *Phoenix dactylifera* fruit flesh per kg of the mammal per day.

In one embodiment of the method, the cancer is breast cancer or liver cancer.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
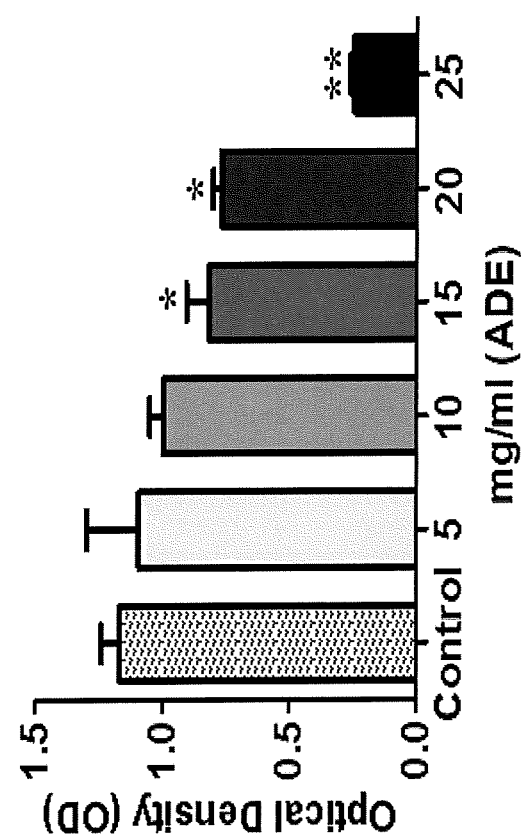
FIG. 1 is a graph showing the inhibition of HepG2 cell proliferation upon treatment with 5-25 mg/mL of Ajwa Date Extract (ADE) for a period of 48 h.

The present disclosure will be better understood with reference to the following definitions. As used herein, the words "a" and "an" and the like carry the meaning of "one or more." Within the description of this disclosure, where a numerical limit or range is stated, the endpoints are included unless stated otherwise. Also, all values and subranges within a numerical limit or range are specifically included as if explicitly written out. Unless defined otherwise, all technical and scientific terms used herein have the same meaning as commonly understood to one of ordinary skill in the art.

As used herein, "compound" refers to a chemical entity, whether in the solid, liquid, gaseous, or supercritical fluid phase, and whether in a crude mixture or purified and isolated.

The term "composition," as used herein, refers to two or more chemical entities that are mixed together to comprise a homogenous or heterogeneous solid, liquid, or gas.

The phrases "pharmaceutically acceptable carrier" or "pharmaceutically acceptable excipient" as used herein mean a pharmaceutically acceptable compound, composition, or vehicle, such as a liquid or solid filler, diluent, binder, manufacturing aid (e.g., lubricant, talc magnesium, calcium or zinc stearate, or steric acid), or solvent encapsulating material, involved in carrying or transporting a compound from one organ, or portion of the body, to another organ, or portion of the body. Each carrier or excipient must be "acceptable" in the sense of being compatible with the other ingredients of the formulation and not injurious to the mammal.

As defined herein, "extraction," refers to a separation process where an extracting gas, liquid, and/or supercritical fluid is brought into contact with a composition whereby a compound from the composition becomes homogeneously or heterogeneously dispersed in the extracting gas, liquid, and/or supercritical fluid. Preferably, "extraction" refers to the physical transfer of a compound from the composition and into the extracting gas, liquid, and/or supercritical fluid, and either a portion or the entire compound is transferred. However, in some cases reagents may be used to react with or digest a part of the composition in order to release a compound. For example, a cellulase enzyme may be used to break up a composition comprising a cellulose matrix, in order to release compounds retained within. As defined herein, an "extract" refers to one or more compounds separated from a composition by an extraction process.

As used herein, the fruits of the plant species denoted by *Phoenix dactylifera* or *Phoenix dactylifera* L. are also referred to as "dates." "Ajwa dates" are the dates from the Ajwa cultivar of a *Phoenix dactylifera* plant.

According to a first aspect, the present disclosure relates to a method for treating a cancer in a mammal comprising administering a therapeutically effective dose of an extract of a *Phoenix dactylifera* fruit flesh to the mammal. Unless otherwise noted, "the extract" refers to an extract of a *Phoenix dactylifera* fruit flesh, and "the fruit flesh" refers to the flesh of one or more dates. A "therapeutically effective dose" refers to an amount of the extract being administered which will relieve to some extent one or more of the symptoms of the cancer being treated. In another embodiment, a "therapeutically effective dose" refers to the amount which has the effect of inhibiting (that is, slowing to some extent, or preferably stopping) cancer cell growth or proliferation. Similarly, the phrase "treat a cancer in a mammal" refers to administering a therapeutically effective dose of the extract to a mammal.

As used herein, the terms "treat", "treatment", and "treating," in the context of the administration of a therapeutically effective dose of the extract to a mammal, refer to the reduction or inhibition of the progression and/or duration of a cancer, the reduction or amelioration of the severity of the cancer, and/or the amelioration of one or more symptoms thereof resulting from the administration of one or more therapies. "Treating" or "treatment" of the cancer includes preventing the cancer from occurring in a subject that may be predisposed to the cancer but does not yet experience or exhibit symptoms of the cancer (prophylactic treatment), inhibiting the cancer (slowing or arresting its development), ameliorating the cancer, providing relief from the symptoms or side-effects of the cancer (including palliative treatment), and relieving the cancer (causing regression of the cancer). With regard to the cancer, these terms simply mean that one or more of the symptoms of the cancer will be reduced. Such terms may refer to one, two, three, or more results following the administration of one, two, three, or more therapies: (1) a stabilization, reduction (e.g. by more than 10%, 20%, 30%, 40%, 50%, preferably by more than 60% of the population of cancer cells and/or tumor size before administration), or elimination of the cancer cells, (2) inhibiting cancerous cell division and/or cancerous cell proliferation, (3) relieving to some extent (or, preferably, eliminating) one or more symptoms associated with a pathology related to or caused in part by unregulated or aberrant cellular division, (4) an increase in cancer-free, relapse-free, progression-free, and/or overall survival, duration, or rate, (5) a decrease in hospitalization rate, (6) a decrease in hospitalization length, (7) eradication, removal, or control of primary, regional and/or metastatic cancer, (8) a stabilization or reduction (e.g. by at least 10%, 20%, 30%, 40%, 50%, 60%, 70%, preferably at least 80% relative to the initial growth rate) in the growth of a tumor or neoplasm, (9) an impairment in the formation of a tumor, (10) a reduction in mortality, (11) an increase in the response rate, the durability of response, or number of patients who respond or are in remission, (12) the size of the tumor is maintained and does not increase or increases by less than 10%, preferably less than 5%, preferably less than 4%, preferably less than 2%, (13) a decrease in the need for surgery (e.g. colectomy, mastectomy), and (14) preventing or reducing (e.g. by more than 10%, more than 30%, preferably by more than 60% of the population of metastasized cancer cells before administration) the metastasis of cancer cells.

As defined here, the fruit flesh is the peel and/or the pulp of one or more dates; preferably the fruit flesh is both peel and pulp. The peel may also be called the skin or epicarp and may be considered the outer 0.5-2 mm, preferably 0.7-1.5 mm layer of a date. The pulp, also called mesocarp, is the part of the date between the peel and the endocarp surrounding the pit. The fruit flesh may or may not include the endocarp. The pit may also be called a seed or kernel. The pulp and peel may make up 75-95 wt %, preferably 80-92 wt % of the total weight of the date.

In one embodiment, the fruit flesh may be from a date harvested from a *Phoenix dactylifera* plant within 3 months, preferably within 3 weeks. In another embodiment, the fruit flesh may be from a date stored in an airtight bag or container in a refrigerator, a freezer, or at room temperature for at least one month, or at least three months, or at least one or two years from the time of harvest. In another embodiment, the fruit flesh may be from a date harvested from a *Phoenix dactylifera* plant within 96 hours, preferably within 48 hours.

On a per 100 g basis, a dried date fruit flesh may have a moisture content of 7-30 g, a fatty acid content of 0.1-1.4 g, a protein content of 1.1-4.8 g, a carbohydrate content of 52-89 g (which includes 13-49 g fructose, 17-53 g glucose, and 0.5-34 g sucrose), a soluble fiber content of 0.4-1.3 g, an insoluble fiber content of 3-7.4 g, a magnesium content of 31-160 mg, a calcium content of 5-190 mg, a potassium content of 290-512 mg, an ascorbic acid content of 0.4-16 mg, and a total phenolic compound content of 3.9-23 mg. Of the phenolic compounds, a dried date fruit flesh may have 0.012-0.027 mg caffeic acid, 0.5-1.27 mg protocatechuic acid, 0.044-0.19 mg chlorogenic acid, and 0.41-0.83 mg syringic acid per 100 g dry weight fruit flesh. The weight ratio of glucose to fructose may range from 1.03:1-1.32:1

The *Phoenix dactylifera* plant may be a cultivar or variety such as Ajwa, Medjool, Mishriq, Zaghloul, Sukkary, Rotab, Piarom, Migraf, Lulu, Khalasah, Kandrawi, Honey, Holwah, Empress, Deglet Noor, Al-Khunaizi, Thoori, Rabi, Mozafati, or some other cultivar or variety. Preferably, the fruit flesh comes from the Ajwa cultivar, and may also be spelled as Ajwah.

Ajwa dates may be distinguished over other date cultivars given their higher total phenolic content of 21-23 mg phenolic compounds per 100 g dry weight. Of particular phenolic compounds, Ajwa dates may have 0.025-0.027 mg caffeic acid, 1.16-1.27 mg protocatechuic acid, 0.18-0.19 mg chlorogenic acid, and 0.81-0.83 mg syringic acid per 100 g dry weight fruit flesh, which are levels higher than typical date cultivars. Ajwa dates may also have calcium, phosphorus, and magnesium levels of 180-190 mg, 450-500 mg, and 120-160 mg, respectively, per 100 g dry weight fruit flesh, and these three minerals are at levels higher than most other date cultivars. Ajwa dates may also have an ascorbic acid concentration of 0.85-0.95 mg per 100 g fresh weight fruit flesh, which is lower compared with other date cultivars. The weight ratio of glucose to fructose in Ajwa dates may be 1.04:1-1.06:1.

In an alternative embodiment, the fruit flesh may not be from a fruit of a *Phoenix dactylifera* plant but some other fruit of a plant within the *Phoenix* genus, including, but not limited to *Phoenix acaulis, Phoenix andamanensis, Phoenix atlantica, Phoenix caespitosa, Phoenix canariensis, Phoenix loureiroi, Phoenix paludosa, Phoenix pusilla, Phoenix reclinata, Phoenix roebelenii, Phoenix rupicola, Phoenix sylvestris, Phoenix zeylanica*, or *Phoenix theophrasti*. In another alternative embodiment, the fruit flesh may be from a fruit of a different palm plant, such as an *Elaeis guineensis* plant (African oil palm), an *Areca catechu* (areca palm), or an *Attalea maripa* (maripa palm).

In an alternative embodiment, an extract may be formed from a *Phoenix dactylifera* plant part that is not the fruit flesh, for example, an extract may be made from a leaf, a stem, a palm heart, a spine, a sheath, a flower, a nectar, a pollen, a sap, or a root.

In one embodiment of the method, the extract is made by contacting a *Phoenix dactylifera* fruit flesh with an organic solvent, and the organic solvent is methanol, ethanol, 1-propanol, 2-propanol, 1-butanol, 2-butanol, tert-butyl alcohol, ethyl acetate, acetone, or acetonitrile. Preferably the organic solvent is methanol, ethanol, 2-propanol, or acetone. More preferably the organic solvent is methanol, ethanol, or 2-propanol. In a preferred embodiment, the organic solvent is methanol. In other embodiments, solvents such as carbon tetrachloride, chloroform, tetrachloroethylene, diethyl ether, ethylene glycol, propylene glycol, glycerol, diethyl ether, hexane, benzene, dimethyl sulfoxide (DMSO), dimethylformamide (DMF), tetrahydrofuran (THF), ethyl acetate, hexane, cyclohexane, heptane, decane, benzene, 1,4-dioxane, iso-octane, n-octane, nonane, toluene, or some other solvent may be used.

In a further embodiment, where the extract is made by contacting a *Phoenix dactylifera* fruit flesh with an organic solvent, the *Phoenix dactylifera* fruit flesh is ground, blended, or cut. The fruit flesh may be subjected to a blender, food processor, mandolin slicer, deli slicer, grinder, press, grater, shredder, juice extractor, shredder, extruder, sonicator, mortar and pestle, knife, scissors, mallet, and the like. In another embodiment, a person may smear or crush the fruit flesh with his or her hands. Preferably the pit and/or stem of the date is removed before the extraction, or before the grinding, blending, or cutting. However, in another embodiment, the pit and/or stem is not removed from the date. In one embodiment, the grinding, blending, or cutting is done while the fruit flesh is in contact or submerged in the organic solvent or other extraction media. For example, the fruit flesh may be placed in a blender with a volume of methanol, and then blended with the methanol.

The fruit flesh may be dried before the extraction and/or dried before the grinding, blending, or cutting. A dried fruit flesh may have a water content of 0.1-20 wt %, preferably 0.5-15 wt %, more preferably 0.8-10 wt % in relation to the total fruit flesh weight. A dried fruit flesh may be from a date in a tamr stage of maturity (i.e., darkened, and about 29-21 weeks post-pollination), or the dried fruit flesh may be from a date in a different maturity stage that has undergone drying by sunlight, a desiccator, a freeze dryer, or dry air. In another embodiment, the fruit flesh may have a higher water content, such as 30-90 wt %, preferably 40-70 wt % relative to a total weight of the fruit flesh, and may come from a date in a rutab or khalaal maturity state, which may be a date 19-25 weeks or 25-29 weeks after pollination, respectively. The fruit flesh may come from dates considered soft, semi-dry, or dry. In an alternative embodiment, fruit flesh may come from earlier fruiting stages, such as Hanabauk or Kimri, which are about 1-5 weeks and 6-19 weeks post-pollination, respectively.

In an alternative embodiment, one or more components may be removed before contacting with the organic solvent. For example, a soft date may be juiced with a juicer, or juiced by blending and then straining out large solids. This straining may decrease the total fiber content by 30-80% or 60-95% compared to the total fiber content of the date before the juicing. Then, the juice may be contacted with the organic solvent. In another alternative embodiment, a date may undergo some other processing step, such as an enzymatic digestion, or a date may be soaked or heated in water or milk to soften the fruit flesh.

In one embodiment, water may be mixed with the organic solvent, and the mixture may be used as an extraction medium. The water may be tap water, distilled water, bidistilled water, deionized water, deionized distilled water, reverse osmosis water, and/or some other water. In one embodiment, the water is bidistilled to eliminate trace metals. Preferably the water is bidistilled, deionized, deionized distilled, or reverse osmosis water and at 22-27° C. has a conductivity of less than 10 $\mu S \cdot cm^{-1}$, preferably less than 1 $\mu S \cdot cm^{-1}$, a resistivity greater than 0.1 M$\Omega \cdot$cm, preferably greater than 1 M$\Omega \cdot$cm, more preferably greater than 10 M$\Omega \cdot$cm, a total solid concentration less than 5 mg/kg, preferably less than 1 mg/kg, and a total organic carbon concentration less than 1000 µg/L, preferably less than 200 µg/L, more preferably less than 50 µg/L.

Where water and one or more organic solvents are used together as the extraction medium, the extraction medium may comprise 30-99 wt %, preferably 50-90 wt %, more preferably 60-80 wt % organic solvent based on the total extraction medium weight. For example, an extraction medium may comprise 75-80 wt % methanol and 20-25 wt % water. In other embodiments, the extraction medium may comprise 1-70 wt %, preferably 10-50 wt %, more preferably 20-40 wt % of one or more organic solvents relative to the total extraction medium weight. The water and one or more organic solvents may be miscible, partially miscible, or immiscible. Where two organic solvents are used, for example, methanol and ethanol, they may have mass ratios of 10:1-1:10, preferably 5:1-1:5, more preferably 2:1-1:2 with each other. In one embodiment, water may not be used in the extraction medium; however, water may transfer from an Ajwa Date fruit flesh to the extraction medium.

In a further embodiment, where the extract is made by contacting a *Phoenix dactylifera* fruit flesh with an organic solvent, a weight ratio of the *Phoenix dactylifera* fruit flesh to the organic solvent is 1:1.5-1:3, preferably 1:1.8-1:2.8, more preferably 1:2.1-1:2.5. However, in other embodiments, much more *Phoenix dactylifera* fruit flesh may be used, providing a weight ratio of the *Phoenix dactylifera* fruit flesh to the organic solvent of 1:1-1.5:1, or 1.5:1-2.5:1. In another embodiment, much more organic solvent may be used, for instance, providing the weight ratio of 1:2.8-1:4, or 1:4-1:8. In one embodiment, a fraction of the organic solvent volume to the *Phoenix dactylifera* fruit flesh weight is 1-5 L/kg, preferably 2-4 L/kg, more preferably 2.5-3.5 L/kg.

In a further embodiment, where the extract is made by contacting a *Phoenix dactylifera* fruit flesh with an organic solvent, the *Phoenix dactylifera* fruit flesh is ground, blended, or cut. The fruit flesh may be put in or subjected to a blender, food processor, mandolin slicer, deli slicer, grinder, press, grater, shredder, juice extractor, shredder, extruder, sonicator, mortar and pestle, knife, scissors, grinding media, blade, mallet, and the like. In another embodiment, a person may smear or crush the fruit flesh with his or her hands. In a preferred embodiment, the fruit flesh is ground with a mortar and pestle. Preferably the pit and/or stem of the Ajwa Date is removed before the extraction, or before the grinding, blending, or cutting. However, in another embodiment, the pit and/or stem is not separated from the fruit flesh. In one embodiment, the grinding, blending, or cutting is done while the fruit flesh is in contact with or submerged within the organic solvent. For example, the fruit flesh may be placed in a blender with a volume of methanol, and then blended with the methanol.

The fruit flesh may be dried, before the extraction or before the grinding, blending, or cutting. The dried fruit flesh may have a water content of 0.1-20 wt %, preferably 0.5-15 wt %, more preferably 0.8-10 wt % in relation to the total fruit flesh weight prior to the drying. A dried fruit flesh may be from a date in a tamr stage of maturity, or may be from a date in a different maturity stage that has undergone drying by sunlight, a desiccator, or warm air. In another embodiment, the fruit flesh may have higher water content, such as 30-90 wt %, preferably 40-70 wt % relative to a total weight of the fruit flesh, and may come from a date in a rutab or khalaal maturity state. The fruit flesh may come from dates considered soft, semi-dry, or dry.

In a further embodiment, where the extract is made by contacting a *Phoenix dactylifera* fruit flesh with an organic solvent, the contacting is done for 12-96 h, preferably 24-36 h, more preferably 35-55 h at 20-30° C., preferably 22-29° C., more preferably 23-28° C. In other embodiments, a fruit flesh that is finely ground, blended, or cut may be contacted for a shorter amount of time, such as 6-10 h, or 3-6 h, due to the fruit flesh having a larger surface area to volume ratio. Preferably the contacting may be done with the organic solvent confined in a closed vessel or container, such as a capped bottle, a covered beaker or flask, a bag, or a covered mixing tank. The closed vessel may not necessarily provide an airtight seal, and may or may not have a headspace of air, or an inert gas such as nitrogen or argon. The fruit flesh may be left to soak in the solvent without perturbing or agitating the solvent. However, in one embodiment, the vessel or container may be rocked, shaken, rolled, sonicated, or moved to agitate the solvent. In other embodiments, the solvent may be stirred with a stir bar, impeller, paddle, rod, or blade. In another embodiment, the solvent may be heated, for instance to 30-60° C., or 30-40° C., or 40-50° C., or 50-60° C. In another embodiment, the solvent may be refluxed with the fruit flesh. In these embodiments where the organic solvent and fruit flesh are heated at temperatures greater than 30° C., they may be contacted for a shorter amount of time, such as 6-10 h, or 3-6 h. The heating may be by a hot plate, a submerged heating coil, a heated bath, a bath sonicator, or a microwave oven. In one embodiment, the fruit flesh and the solvent are contacted at atmospheric pressure. However, in another embodiment, the fruit flesh and organic solvent may be exposed to higher pressures, such as an absolute pressure of 1.01-20 atm, preferably 1.02-5 atm. In a related embodiment, a supercritical fluid may be used as the solvent, for example, supercritical fluid $CO_2$ may be formed at temperatures above 31.5° C. and at absolute pressures above 73 atm.

In another embodiment, a frozen fruit flesh (such as that removed from a freezer and at a temperature of −20-−5° C. or colder) may be added to an organic solvent at 20-30° C., and the fruit flesh may eventually warm to 20-30° C. or ambient temperatures.

Contacting the fruit flesh with the organic solvent leads to an extract of one or more compounds dispersed in the organic solvent, forming a liquid mixture. In one embodiment, every kg of fruit flesh leads to a total extract mass of 1-400 g, preferably 5-300 g. Following the contacting, solids of the fruit flesh may be removed from the liquid mixture. This removing may be by filtering, straining, centrifugation, or distillation. In one embodiment, the solids may be large enough to be easily removed with forceps. In another embodiment, the fruit flesh may be placed in a strainer, basket, or mesh bag, which may be lowered into and then lifted out of the liquid mixture. In one embodiment, the fruit flesh solids may be filtered with Whatman filter paper or a paper coffee filter. In one embodiment a Whatman #1 filter paper is used. The filtering may be done with or without an applied vacuum or external pressure. Other types of filters may be used, such as a porous metal disk, a fine wire mesh, a ceramic filter, a capillary filter, or a polymer membrane comprising a polymer such as polypropylene, polyethylene, nylon, polyvinylidene fluoride, or polyethersulfone. A filtered extract may be in the form of solids having diameters or widths of 0.1-15 µm, preferably 0.5-13 µm, more preferably 1-11 µm, with the solids suspended in the liquid extraction medium. In other embodiments, solids may float on the surface or sink to the bottom of the liquid extraction medium. Additionally, a filtered extract may contain dissolved compounds in the form of separated molecules, atoms, or ions.

In one embodiment, the filtered extract may be centrifuged at 1,000-10,000×g, preferably 2,000-6,000×g, more preferably 3,000-5,000×g for 5-60 min, preferably 10-45 min, more preferably 12-30 min to further remove solid compounds. However, in one embodiment, the filtered extract may not be centrifuged. In another embodiment, the extract and the extraction medium may be centrifuged before the filtering. In one embodiment, the extract and the extraction medium may be filtered, centrifuged, and then filtered again.

In one embodiment, the extract may be dried after filtering in order to remove the organic solvent. The drying may be accomplished with a rotary vacuum, a spray tower, a freeze dryer, a flow of heated air, a flow of dry air or gas, a dryer, a cylindrical dryer, a zeolite dryer, an oven, a desiccator, a heat lamp, or a vacuum desiccator. In other embodiments, some solvents may evaporate quickly enough on their own at ambient conditions in an uncovered or vented container, with no active drying step required.

However, in one embodiment, the extract is not dried, or only a portion of a solvent is removed in order to concentrate the extract. For example, where the solvent is ethanol or water, the mixture of the extract and solvent may be administered with or without concentrating the extract. In other embodiments, a filtered or partially-dried extract may be washed with a liquid to further remove a liquid extraction medium.

A dried extract may be in the form of a powder with particles having diameters as mentioned above for the filtered extract, though in some embodiments, the particles may stick together upon drying or further processing, and form particle sizes of 15-600 µm, 50-400 µm, or 60-300 µm. In other embodiments, a dried extract may be in the form of a viscous film. A dried extract may be stored in a freezer for later use, such as a freezer with a temperature of −90-−5° C., preferably −85-−75° C., or −35-−15° C. Alternatively, a dried extract may be stored on ice or in a refrigerator at 2-5° C.

In one embodiment, the extract may comprise one or more compounds such as sucrose, glucose, fructose, cellulose, hemicellulose, lignin, ligno-cellulose, soluble fiber, insoluble fiber, protein, amino acid, palmitic acid, capric acid, caprylic acid, linoleic acid, lauric acid, pelargonic acid, myristic acid, invertase, polygalacturonase, pectinesterase, cellulase, polyphenol oxidase, citric acid, ascorbic acid, malic acid, oxalic acid, lutein, vitamin A, vitamin $B_1$, vitamin $B_2$, niacin, potassium, α-carotene, β-carotene, calcium, iron, copper, magnesium, sulphur, phosphors, water, p-coumaric acid, chlorogenic acid, ferulic acid, nucleic acid, cyanindin, catechin, caffeic acid, hydrocaffeic acid, gallic acid, ellagic acid, vanillic acid, protocatechuic acid, syringic acid, p-hydroxybenzoic acid, sinapinic acid (sinapic acid), dactylifric acid (3-O-caffeoylshikimic acid), a β-glucan (such as β-D-glucan), a flavonoid, a procyanidin, or a polyphenol. Preferably, the extract comprises p-coumaric acid, ferulic acid, sinapinic acid, a β-glucan, a flavonoid, a procyanidin, or a polyphenol. A flavonoid of the extract may be a procyanidin, quercetin, apigenin, luteolin, or myricetin. The extract may comprise other carbohydrates, enzymes, organic acids, fatty acids, vitamins, minerals, dietary fibers, phytochemicals, antioxidants, salts, or volatile compounds. The extract may comprise any of the above compounds at a weight percentage of 0.00001-0.0001 wt %, 0.0001-0.001 wt %, 0.001-0.01 wt %, 0.01-0.1 wt %, 0.1-0.5 wt %, 0.5-1.0 wt %, 1.0-10 wt %, 10-20 wt %, 20-30 wt %, 30-40 wt %, 40-50 wt %, 50-60 wt %, 60-70 wt %, 70-80 wt %, 80-90 wt %, or 90-99.9 wt % relative to a total weight of the extract.

Preferably, after the drying, the extract contains less than 5 wt %, preferably less than 3 wt %, more preferably less than 1 wt %, even more preferably less than 0.1 wt % of the extracting medium relative to a total weight of the extract. In one embodiment, the extract may contain a compound, such as a protein, from a yeast or other microorganism present on the fruit flesh. The types of compounds and their amounts in the extract may vary across different samples of date fruit flesh based on factors including, but not limited to, date maturity, environmental conditions such as soil nutrients, sun, hydration, and temperature, age of plant, and cultivar or variety of plant within the *Phoenix dactylifera* species. Additionally, the types of compounds and their amounts in the extract may vary across date fruit flesh based on the different preparation methods, extraction reagents, and parameters as described previously.

In a preferred embodiment, the extract and the date fruit flesh have different compositions. For instance, in one embodiment, the extract may have a higher weight percentage of phenolic compounds relative to a total weight of the extract, as compared to a weight percentage of phenolic compounds relative to a total weight of the date fruit flesh. Here, the weight percentage of one or more phenolic compounds may be increased by 50-300%, preferably 60-250%, more preferably 70-200%. In another embodiment, the extract may have a lower weight percentage of carbohydrates, insoluble fiber, or fatty acids with respect to the total weight of the extract as compared to the weight percentage of the same compounds with respect to the total weight of the date fruit flesh. Here, the weight percentage of carbohydrates, insoluble fiber, or fatty acids in the extract may be 20-98% lower, preferably 30-95% lower, more preferably 40-90% lower.

In one embodiment, the extract may be prepared into a composition, such as a pharmaceutical composition or a food product, in solid, semi-solid (e.g. gel), or liquid dosage forms. The composition may comprise a pharmaceutically acceptable excipient, a pharmaceutically acceptable carrier, a food product, or an antioxidant. Methods of preparing such compositions include a step of bringing into association the extract with a pharmaceutically acceptable carrier or excipient and, optionally, one or more accessory ingredients. In general, the pharmaceutical composition may be prepared by uniformly and intimately bringing into association the extract with liquid carriers, or finely-divided solid carriers, or both, and then, if necessary, shaping a product. This contacting may be done before, during, or after the extracting, filtering, centrifuging, and/or drying.

A solid composition may comprise the extract at a weight percentage of 5-98 wt %, preferably 30-90 wt %, more preferably 40-80 wt %, relative to the total solid composition weight, with the remaining composition comprising pharmaceutical carriers, excipients, or other ingredients. In solid dosage forms for oral administration (including but not limited to capsules, tablets, pills, powders, and granules), the extract may be mixed with one or more pharmaceutically acceptable carriers or excipients such as: (1) fillers or extenders, such as starches, lactose, sucrose, glucose, mannitol, and silicic acid; (2) binders, such as carboxymethylcellulose, alginate, gelatin, polyvinyl pyrrolidone, and sucrose; (3) humectants, such as glycerol; (4) disintegrating agents, such as alginate, calcium carbonate, potato or tapioca starch, silica, and sodium carbonate; (5) solution retarding agents, such as paraffin; (6) absorption accelerators, such as quaternary ammonium compounds; (7) wetting agents, such as acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. In the case of a solid form, the dried extract may be mixed with one of the above compounds and pressed to form a pellet, pill, or tablet. In another embodiment, a dried extract may be directly placed in a capsule, with or without additional compounds. A solid form may be formulated for quick release or a controlled release following oral administration. In this context, "a controlled release" refers to a delay for an effective compound of the extract to be released into a mammal, and this delay is created by one or more pharmaceutically acceptable carriers or excipients present in the composition. Here, half of the total weight of this effective compound is released no sooner than 1-36 hours, preferably 2-24 hours, more preferably 3-12 hours after oral administration.

In one embodiment, a liquid or gel composition is formed by reconstituting dried extract powder to 0.1-70 wt %, preferably 1-60 wt %, more preferably 10-50 wt % of the total composition weight. Preferably the reconstituting leads to a homogeneous mixture of the extract in the liquid or gel.

Liquid dosage forms for oral administration include pharmaceutically acceptable emulsions, microemulsions, solutions, suspensions, syrups, and elixirs. The liquid dosage forms may also contain inert diluents commonly used in the art, such as, for example, water or other solvents, solubilizing agents and emulsifiers, such as ethyl alcohol, ethyl carbonate, ethyl acetate, benzyl alcohol, benzyl benzoate, propylene glycol, 1,3-butylene glycol, oils (in particular, cottonseed, corn, peanut, sunflower, soybean, olive, castor, and sesame oils), glycerol, tetrahydrofuryl alcohol, corn syrup, polyethylene glycols and fatty acid esters of sorbitan, and mixtures thereof.

In one embodiment, the extract may be administered as part of a composition comprising an isotonic solution. In this embodiment, the extract may be present as 0.01-10 wt %, preferably 0.1-5 wt %, more preferably 0.5-2 wt % of the total composition weight. Here, the isotonic solution may be buffered, such as phosphate buffered saline, lactated Ringer's solution, acetated Ringer's solution, or a DSNS intravenous sugar solution, and may have a pH of 7.2-7.5, or about 7.4. The composition may be formulated for intravenous or intramuscular administration.

Semi-solid (e.g. gel) dosage forms may be used for topical administration and may include sprays, ointments, pastes, creams, lotions, gels, and patches. These forms may further include pharmaceutically acceptable carriers or excipients such as animal and vegetable fats, oils, waxes, paraffins, starch, tragacanth, cellulose derivatives, polyethylene glycols, silicones, bentonites, silicic acid, talc, acrylate polymers, isopropyl myristate, carbomer, and zinc oxide.

A gel for oral administration may be produced by mixing the extract with water and a gelling agent or thickening agent, such as starch, starch derivative, vegetable gum, agar, carrageenan, gelatin, albumen, pectin, fumed silica, or carbomer. In another embodiment, a gel may not require water, for instance, a gel may be formed by mixing the extract with glycerol, coconut oil, palm oil, or some other saturated dietary oil. A gel may also include ingredients similar to those used for the orally administered liquid composition. The gel may have a viscosity of 1,000-90,000 cp, preferably 3,000-75,000 cp, more preferably 5,000-50,000 cp. In other embodiments, semi-solids that are not gels, such as wet foam, may be formed with the extract. A gel for oral administration may be administered as a gel directly into the mammal's mouth, or may be packaged into a capsule.

In one embodiment of the method, the extract is administered as a part of a composition which further comprises an antioxidant. The antioxidant may be melatonin, lutein, α-carotene, β-carotene, astaxanthin, tocotrienol, tocopherol, ascorbic acid, gallic acid, ellagic acid, or lycopene. Preferably the antioxidant is melatonin, astaxanthin, tocotrienol, tocopherol, or lycopene. In one preferred embodiment, the antioxidant is melatonin. The weight ratio of the antioxidant to the extract may be 1:65,000-1:1, preferably 1:10,000-1:100, more preferably 1:5,000-1:500. However, in other embodiments, the antioxidant may be administered at a greater mass than the extract.

In one embodiment of the method, the extract is administered as a part of a composition which further comprises a food product. The food product may be an ingredient to improve a flavor or appearance of the extract for oral administration, such as sugar, food coloring, non-nutritive sweeteners, preservatives, artificial flavoring, or natural flavoring. In one embodiment, the food product may be a snack or candy, such as dried fruit, a lozenge, fruit leather, yogurt, pudding, a gummy, an energy bar, a candy bar, or a chewing gum. In other embodiments, the food product may be a drink, such as tea, water, milk, smoothie, soft drink, or shake. The extract may also be frozen inside ice cream or a Popsicle. In other embodiments, the food product may be a food that is part of a meal. For example, the extract could be mixed into or sprinkled on soup, vegetables, fruit, bread, cake, rice, porridge, or meat. The extract may be formulated as a condiment, such as a jam or spread. In addition, the extract may be packaged with a food product in different ways. For example, the extract may be packaged in a capsule that can either be swallowed or opened to sprinkle the extract on food. Alternatively, the extract may be packaged as a gel in a squeezable tube, or a syrup in a bottle with a resealable cap. In one embodiment, the extract may be taken orally with a morning meal and an evening meal. The extract may be taken separately at the same time as the meal, or may be mixed into the food of the meal as described above.

In one embodiment of the method, the cancer is breast cancer or liver cancer. However, in other embodiments, the cancer may be colorectal cancer, stomach cancer, skin cancer, prostate cancer, ovarian cancer, testicular cancer, renal cancer, brain cancer, lung cancer, uterine cancer, colon cancer, bladder cancer, esophageal cancer, and pancreatic cancer. The cancer may be an adenocarcinoma, a basal cell carcinoma, a squamous cell carcinoma, a renal cell carcinoma, a ductal carcinoma in situ (DCIS), an invasive ductal carcinoma, a transitional cell carcinoma, a soft tissue sarcoma, or leukemia. Preferably the cancer is an adenocarcinoma. The mammal may be *Homo sapiens sapiens, Pan troglodytes, Bos primigenius, Sus scrofa domesticus, Canis lupus familiaris, Felis catus, Rattus norvegicus, Mus musculus*, or *Equus ferus caballus*. Preferably, the mammal may be *Homo sapiens sapiens*. In an alternative embodiment, the cancer may be in a non-mammal animal, such as a *Gallus gallus*.

A mammal in need of treatment includes a subject already with a cancer, a mammal which does not yet experience or exhibit symptoms of a cancer, and a mammal predisposed to a cancer. In one embodiment, the subject is a person who is predisposed to cancer, e.g. a person with a family history of cancer. African Americans, Jews of Eastern European descent, or a person with: (i) a personal history of colorectal polyps and/or inflammatory bowel disease, (ii) a family history of adenomatous polyps, (iii) an inherited syndrome (Lynch syndrome, Turcot syndrome, Peutz-Jeghers syndrome, MUTYH-associated polyposis), and/or (iv) type 2 diabetes, are at a higher risk of contracting colon cancer. White women or a person with (i) certain inherited genes (e.g. mutated BRCA1, BRCA2, ATM, TP53, CHEK2, PTEN, CDH1, STK11, and PALB2), (ii) radiation to one's chest, and/or (iii) exposure to diethylstilbestrol (DES), are at a higher risk of contracting breast cancer. Asian Americans, Pacific Islanders, or a person with (i) chronic viral hepatitis (Hep-B or Hep-C), (ii) cirrhosis, (iii) type 2 diabetes, (iv) diseases such as tyrosinemia, alphal-antitrypsin deficiency, porphyria cutanea tarda, glycogen storage diseases, wilson disease, and/or (v) chronic exposure to aflatoxins, vinyl chloride, and thorium dioxide (Thorotrast), are at a higher risk of contracting liver cancer. In a preferred embodiment, the mammal in need of treatment may be currently undergoing other forms of treatment for a cacner, for instance, chemotherapy or radiation therapy. In another embodiment, the mammal in need of treatment may be one that has had cancer and is being treated in order to prevent relapse.

In another embodiment, cancer cells may be treated in vitro, for instance, as a way to test the extract under different conditions in a controlled environment or with additional drugs. These cancer cells may come from a biopsy of a mammal, for instance a biopsy of a liver cancer or a breast cancer, or the cells may be from an established cancer cell line, for instance, MDA-MB-231, MCF-7, AU565, BT20, HeLa, HepG2, SNU-475, LH86, Caco-2, NCI-H250, A-498, Eph4 1424.2, SK-MES-1, DU 145, CHLA-02-ATRT, SCC-4, A-253, or some other cancer cell line. Preferably the cancer cell line may be MCF-7 or HepG2. The cells may come from a cancer that formed on its own in a mammal, or may come from a cancer that was formed by chemical induction or radiation. Diethyl nitrosoamine, (DEN), 7,12-dimethylbenz[a]anthracene (DMBA), 12-O-tetradecanoyl-phorbol-13-acetate (TPA), azoxymethane (AOM), or some other carcinogenic compound may be used to chemically induce cancer. Additionally, the cancer cells may be derived from a tumor or cancer cells that were transplanted and allowed to grow in a mammal.

In one embodiment of the method, the therapeutically effective dose is 0.1-5 g, preferably 0.2-3 g, more preferably 0.3-2 g of the extract per kg of the mammal per day. In other embodiments, lower dosages may be effective, such as 0.1-100 mg, preferably 10-50 mg per kg of the mammal per day. In one embodiment, the administration may be split or distributed over a single day. For example, a 1 g per kg per day dose could be split into two separate doses of 0.5 g per kg, and administered at two different times in a day, for example, 8 AM and 7 PM. Or, a 1 g per kg per day dose could be split into four separate doses of 0.25 g per kg, and administered at four different times in a day. In a related embodiment, a daily dose may be a combined dose administered less frequently than every day. For example, a 0.75 g per kg per day dose could be administered as a 1.5 g per kg dose every other day. In certain embodiments, the dose may be continually administered throughout an entire day or a part of a day, such as by transdermal administration or intravenous administration. Where a dose is administered continuously throughout part of the day, it may be administered for 2-18 h, or 4-16 h. In an alternative embodiment, date fruit flesh, not having been contacted with an extraction medium, may be administered orally to provide an equivalent dosing of one or more compounds contained within the date extract.

In one embodiment of the method, the administering is by a mode of oral administration, intravenous administration, topical administration, inhalation spray, rectal administration, topical administration, intradermal administration, transdermal administration, subcutaneous administration, intramuscular administration, intralesional administration, intrapulmonal administration, sublingual administration, or intratumoral administration. Preferably the administering is by oral administration, intravenous administration, intramuscular administration, or intratumoral administration. In one preferred embodiment, the therapeutically effective dose is administered orally.

The concentration of a biomolecule in a sample may be measured with an assay, for example an antibody-based method (e.g. an ELISA). As used herein, the term "antibody-based method" refers to any method with the use of an antibody including, but not limited to, enzyme-linked immunosorbent assay (ELISA), Western blotting, immunoprecipitation (IP), enzyme linked immunospot (ELISPOT), immunostaining, immunohistochemistry, immunocytochemistry, affinity chromatography, and the like. Preferably, an immunoassay, such as a Luminex Multiplex Assay (Life Technologies) may be used. The activity of an enzyme in a sample may be measured by a variation of the above methods, or by a colorimetric assay. The protocol for measuring the concentration of a biomolecule or the activity of an enzyme is known to those of ordinary skill in the art, for example, by performing the steps outlined in commercially available assay kits sold by Sigma-Aldrich, Thermo Fisher Scientific, R & D Systems, ZeptoMetrix Inc., Cayman Inc., Life Technologies, Abcam, Trevigen, Dojindo Molecular Technologies, Biovision, and Enzo Life Sciences.

The term "sample" includes any biological sample taken from the mammal including a cell, tissue sample, or body fluid. For example, a sample may include a skin sample, a cheek cell sample, saliva, or blood cells. A sample can include, without limitation, a single cell, multiple cells, fragments of cells, an aliquot of a body fluid, whole blood, platelets, serum, plasma, red blood cells, white blood cells, endothelial cells, tissue biopsies, synovial fluid, and lymphatic fluid. Preferably, for biomolecule expression levels, the sample is taken from a cancer, and for enzyme activity levels, the sample is taken from a serum.

In preferred embodiments, the concentration of the biomolecule or activity of the enzyme is measured before and after the administration in order to provide a comparison.

In one embodiment of the method, the cancer is breast cancer, and an activity of an enzyme in a serum of the mammal is increased 2%-50%, preferably 10-48%, more preferably 20-45% after the administering compared to an activity prior to the administering. In a related embodiment of the method, the cancer is liver cancer, and an activity of an enzyme in a serum of the mammal is increased 2-110%, preferably 20-100%, more preferably 30-80% after the administering compared to an activity prior to the administering. For both embodiments, the administering may be for a duration of 1-12 months, preferably 1.5-6 months, more preferably 2-4 months. However, enzyme activity levels may have measureable changes after a shorter length of administration, for instance, after 1-3 weeks of administering. The enzyme activity may be measured by taking a blood sample of the mammal before and after the administering. Each blood sample may be centrifuged to separate the serum, and then an assay may measure the enzyme activity in the serum. The assay may use an antibody-based method or some other technique as described earlier. In one embodiment the enzyme is superoxide dismutase (SOD), catalase (CAT), glutathione reductase (GR), glutathione peroxidase (GPx), or some other antioxidant enzyme. Other enzymes may be assayed for activity levels such as methionine synthase reductase, cytochrome c peroxidase, eosinophil peroxidase, lactoperoxidase myeloperoxidase, thyroid peroxidase, deiodinase, iodothyronine deiodinase, or iodotyrosine deiodinase.

In other embodiments, similar changes in enzyme activities may be measured for mammals with other cancers, for example, colon cancer or lung cancer. In addition, enzyme activity levels may change after a shorter length of administration, for instance, after 1-3 weeks.

In one embodiment of the method, the cancer is liver cancer, and after the administering, an IL-2 expression level of the cancer is increased 20-80%, preferably 30-70%, more preferably 40-65% relative to an IL-2 expression level of the cancer before the administering. Alternatively, a G-CSF expression level of the cancer is increased 25-50%, preferably 30-45%, more preferably 32-42% relative to a G-CSF expression level of the cancer before the administering. Alternatively, an MIP-1a expression level of the cancer is increased 30-80%, preferably 35-78%, more preferably 38-75% relative to an MIP-1a expression level of the cancer before the administering. Alternatively, a GM-CSF expression level of the cancer is increased 80-110%, preferably 85-105%, more preferably 90-100% relative to a GM-CSF expression level of the cancer before the administering. In this embodiment, the administering may be by intravenous administration or intratumoral administration. These expression levels as described above or those for other proteins may be measured for breast cancer or for other cancers. Other biomolecules may show a measureable increase, such as the level of total sulfhydryl groups (T-GSH). The administering may decrease levels of other biomolecules, such as the tumor necrosis factor α (TNF-α) level, the concentration of thiobarbituric acid reactive substances (TBARS), or the malondialdehyde (MDA) level. To measure these cytokine expression levels, and levels of other biomolecules, a sample of cellular fluid may be collected by a needle biopsy of a liver tumor, or by culturing cells from a liver tumor and measuring the supernatant or cell lysate after a period of cell growth. The sample may be measured with ELISA, mass spectrometry, or bead-based immunoassay, such as a Luminex fluorescent assay, to produce a relative or absolute value of an expression level. In one embodiment, a cytokine or biomolecule may show a dose dependent response to the amount of date extract administered.

A person having ordinary skill in the art may be able to adjust administration based on the changes in enzyme activity or biomolecule expression levels. For example, a human patient with liver cancer who is administered the date extract at a dosage of 1 g per kg bodyweight per day for 3 months may show an IL-2 expression level increase of 15% as compared to before the administering. The daily dosage may be increased to 2 g per kg bodyweight to cause a desired 30-70% increase in IL-2 expression levels of the cancer. In another example, a human patient with breast cancer who is administered the date extract at a dosage of 1.2 g per kg bodyweight per day for 3 months may show a superoxide dismutase enzyme activity increase of 150% as compared to before the administering. The daily dosage may then be decreased to 0.6 g per kg bodyweight so that the enzyme activity is only increased 20-45% as compared to before the administering. In other embodiments, a percent change in enzyme activity or biomolecule expression levels may warrant modifications to other treatment methods, such as other supplements or a chemotherapy regimen.

In one embodiment, the extract may be administered in conjunction with other forms of cancer treatment, such as radiation therapy or chemotherapy. Preferably the extract may be administered 1-4 weeks or 2-3 weeks before starting a chemotherapy regimen, and the administration would continue throughout the duration of the chemotherapy. The administering may be stopped at the same time as the other cancer treatment, or the extract may be administered indefinitely. It is envisioned that compounds of the extract may work synergistically with chemotherapy drugs. Alternatively, one or more compounds of the extract, such as those previously mentioned, may induce or cause apoptosis in a cancer cell. In other embodiments, one or more compounds of the extract may reduce the effects of oxidative stress caused by a cancer or a side effect of a cancer treatment.

In another alternative embodiment, the extract may be used to prevent or treat other diseases and conditions such as anemia, hypertension, dementia, fatigue, inflammation, stroke, constipation, impotence, arthritis, osteoporosis, atherosclerosis, nausea, seasonal allergic rhinitis, hypercholesterolemia, intestinal disorders, night blindness, headache, or migraine. In an alternative embodiment, the extract may be administered in solid, semi-solid, or liquid forms to treat oxidative damage resulting from other diseases or conditions, for instance, sunburn, diabetes mellitus, hyperglycemia, or metabolic processes. The extract may be used to prevent or relieve oxidative stress caused by tobacco smoke, ozone, air pollution, or other environmental conditions.

According to a second aspect, the present disclosure relates to a method for preventing cancer in a mammal comprising orally administering 0.1 to 5 g of an extract of a *Phoenix dactylifera* fruit flesh per kg of the mammal per day. This method may include any of the previously discussed administration modes, though preferably, the administering is oral, as in a tablet to be swallowed or chewed, or as a food supplement that may be mixed into a beverage or sprinkled on or stirred into solid food. In one embodiment of the method of preventing cancer, the cancer is breast cancer or liver cancer, or the cancer may be any of the previously mentioned cancers or some other cancer. In one embodiment, a person having a family history of cancer, or certain genetic markers for cancer, may take the extract as a preventative measure.

In an alternative embodiment, the extract may not be administered directly to an animal, but may be added to a food product or pharmaceutical compound to delay oxidation and rancidity. This may increase shelf life. For instance, the extract may be mixed with flax seed oil or sunflower seed oil, or sprinkled on dried fish.

The examples below are intended to further illustrate protocols for preparing and using the extract of the date fruit flesh, and are not intended to limit the scope of the claims.

Example 1

Preparation of Ajwa Date Extract

The preparation of the Ajwa Date Extract (ADE) first involved grinding the fruit flesh of Ajwa Dates with the help of a pestle and mortar. This was followed by extraction with methanol (1:3 ratio, weight fruit flesh to volume methanol), using a shaking incubator (Human Lab, Gyeonggi-Do, Korea) at 25° C. for a period of 48 h. The resulting extract was passed through filter paper (Whatman No. 1), and centrifuged at 4000×g for 15 min. The collected supernatant was filtered again, and lyophilized using a lyophilizer (il-Shin Biobase Europe B.V., Kryptonstraat, WR Ede, The Netherlands). The collected powder was divided into aliquots, transferred into 15 mL conical tubes, and stored at −80° C. Different dilutions of the powder in Dulbecco's Phosphate-Buffered Saline with a pH of 7.4 were applied in vitro on MCF-7 and HepG2 carcinoma cells, and applied orally, in vivo, to rats subjected to a chemical induction of breast and liver adenocarcinoma. See Khan F., Ahmed F., Pushparaj P. N., Abuzenadah A., Kumosani T., Barbour E., AlQahtani M., Gauthaman, K., *PLOS ONE,* 11, e0158963 (2016); Hall P. A. et al., *J. Pathol,* 172, 1 (1994)—incorporated herein by reference in its entirety.

Example 2

Dose-dependent Effect of ADE on HepG2 Proliferation

This in vitro experiment shows the dose-dependent anti-cancer activity of the Ajwa Date Extract (ADE) against proliferation of human liver adenocarcinoma cells, known as HepG2, following a previously documented calorimetric protocol. See Mosmann, T., *J. Immunol. Methods,* 65, 55 (1983)—incorporated herein by reference in its entirety. The treatment of HepG2 cell line with 5-25 mg/mL of ADE for 48 h showed significant decrease in the proliferation of liver cancer cells at concentrations >15 mg/mL (FIG. 1).

Example 3

Figure 2:
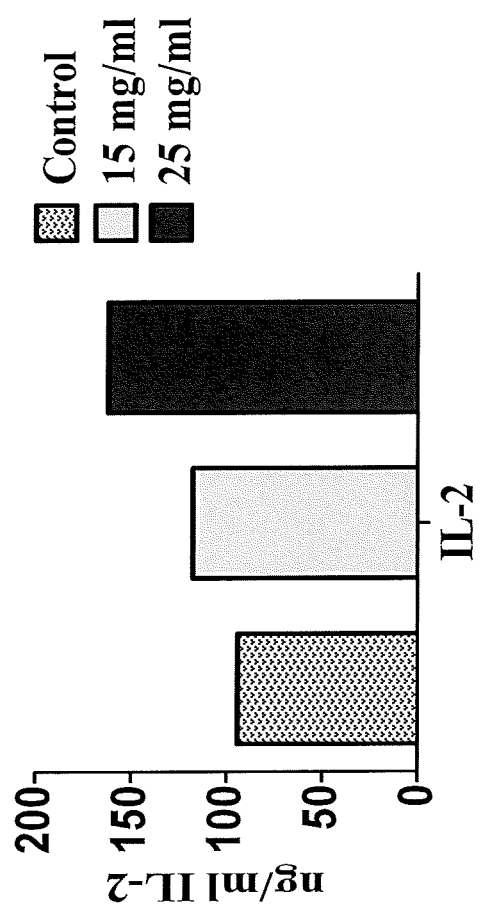
FIG. 2 is a graph showing the dose-dependent effect of ADE on IL-2 expression in HepG2 cells.

Dose Dependent Effect of ADE on Th1 Interleukin-2 Expression Level in HepG2 Cells This in vitro experiment shows a dose-dependent effect of ADE on expression of Th1 Interleukin-2 (IL-2) by HepG2 cells, after 48 h of contact with the ADE. The Th1-IL-2 expression is related to control of these cancer cells. See Rosenberg S. A. et al., *N. Engl. J. Med.,* 316, 889 (1987)—incorporated herein by reference in its entirety. The supernatant of the cells contacted with the ADE was collected and analyzed for 30 plex cytokines assay using a commercial kit (Life Technologies, USA), followed by application of a MAGPIX Luminex instrument. Control cells were not contacted with ADE. The results showed a dose-dependent increase in Th1 cytokine IL-2 expression by the contact of HepG2 cells with 15 and 25 mg/mL of ADE concentrations as compared to the untreated control (FIG. 2).

Example 4

Dose Dependent Effect of ADE on Cytokine Levels in HepG2 Cells

Figure 3:
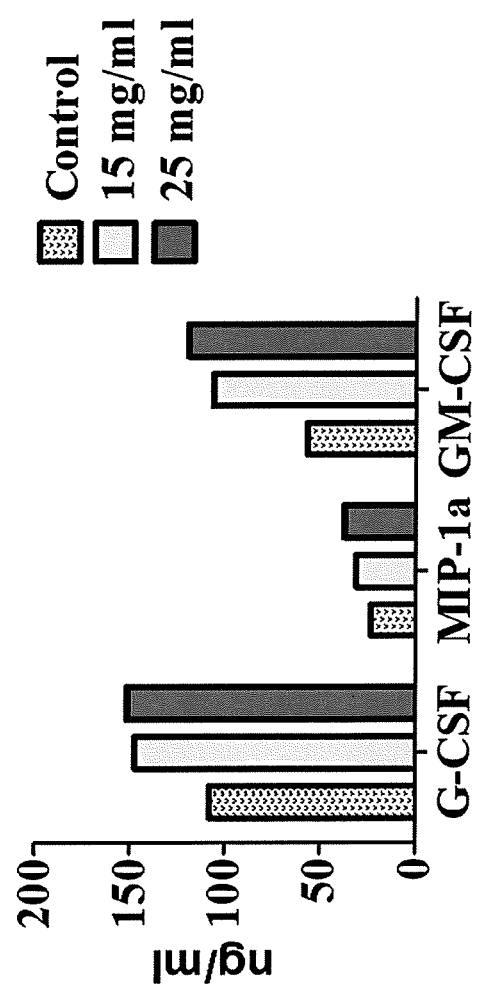
FIG. 3 is a graph showing the effect of different concentrations of ADE on the expression levels of G-CSF, MIP-1a, and GM-CSF in HepG2 cells after 48 h of contact.
Figure 4:
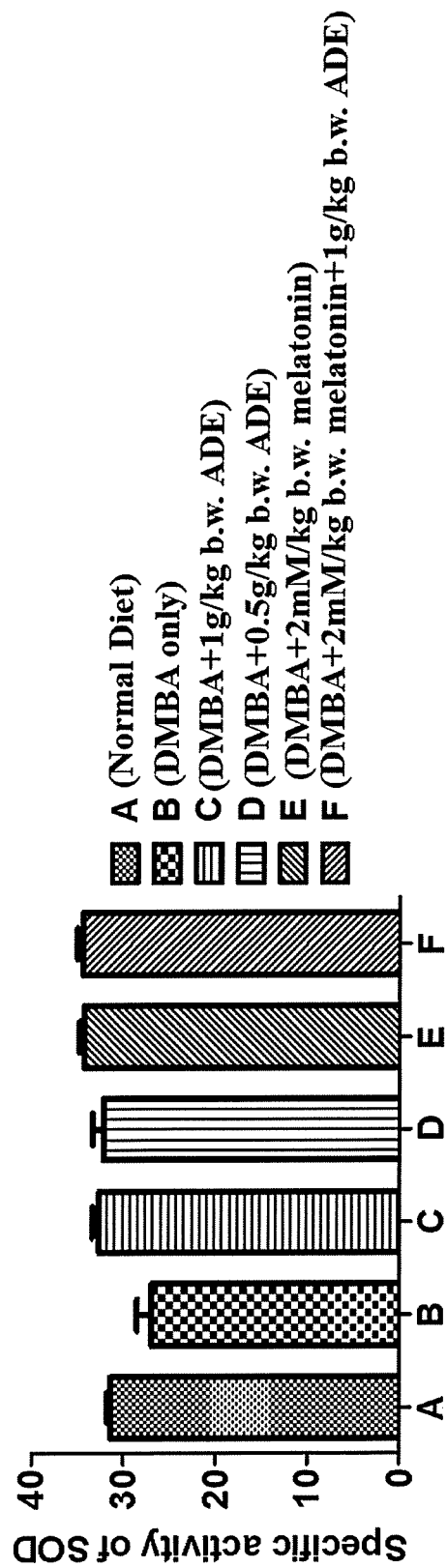
FIG. 4 is a graph showing the effect of ADE and/or melatonin on serum superoxide dismutase (SOD) activity in female Wistar rats having DMBA-induced breast cancer.
Figure 5:
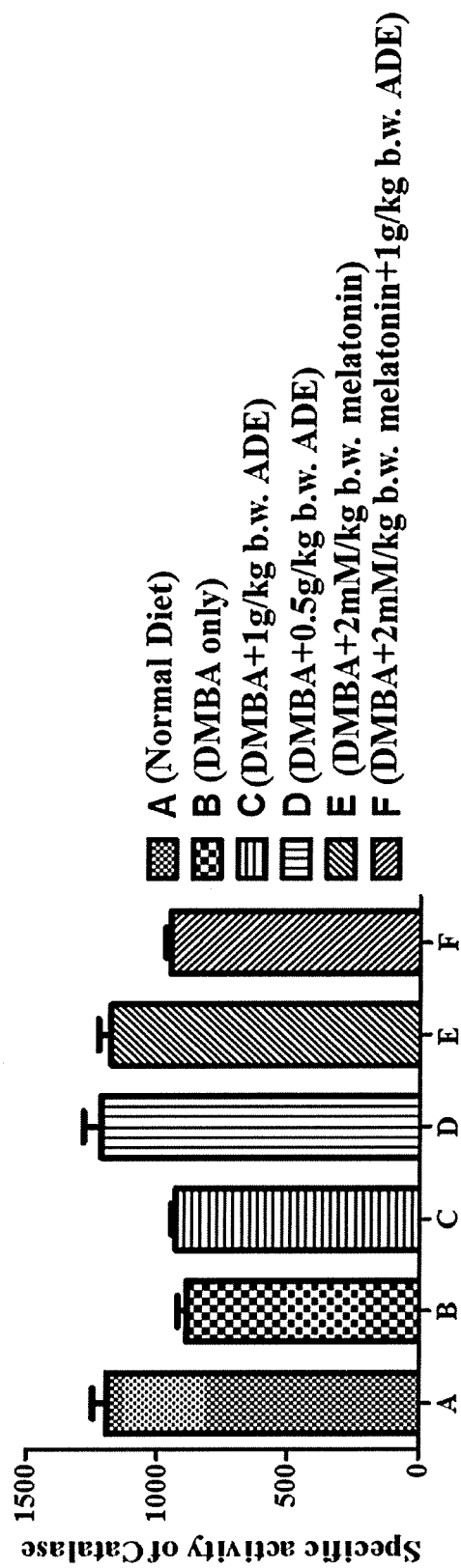
FIG. 5 is a graph showing the effect of ADE and/or melatonin on serum catalase activity in female Wistar rats having DMBA-induced breast cancer.
Figure 6:
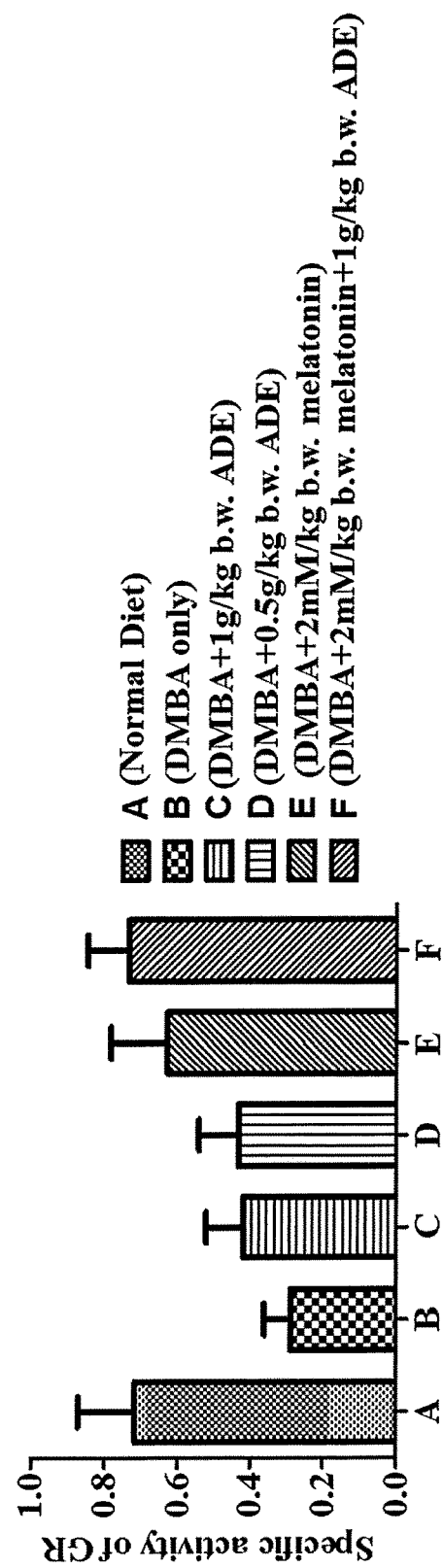
FIG. 6 is a graph showing the effect of ADE and/or melatonin on serum glutathione reductase (GR) activity in female Wistar rats having DMBA-induced breast cancer.
Figure 7:
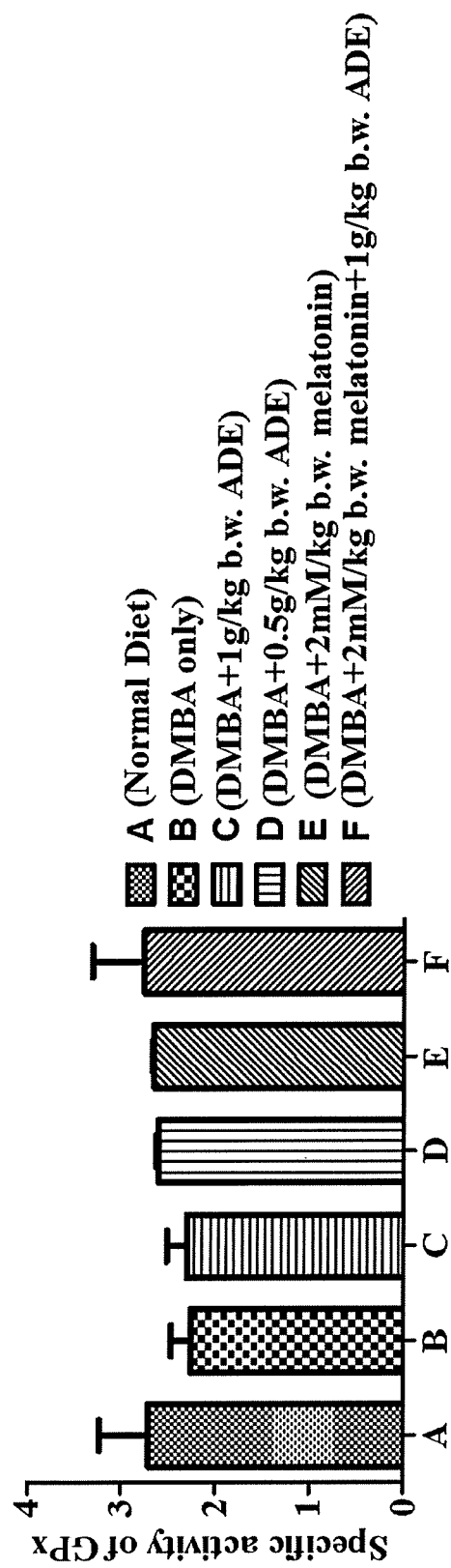
FIG. 7 is a graph showing the effect of ADE and/or melatonin on serum glutathione peroxidase (GPx) activity in female Wistar rats having DMBA-induced breast cancer.
Figure 8:
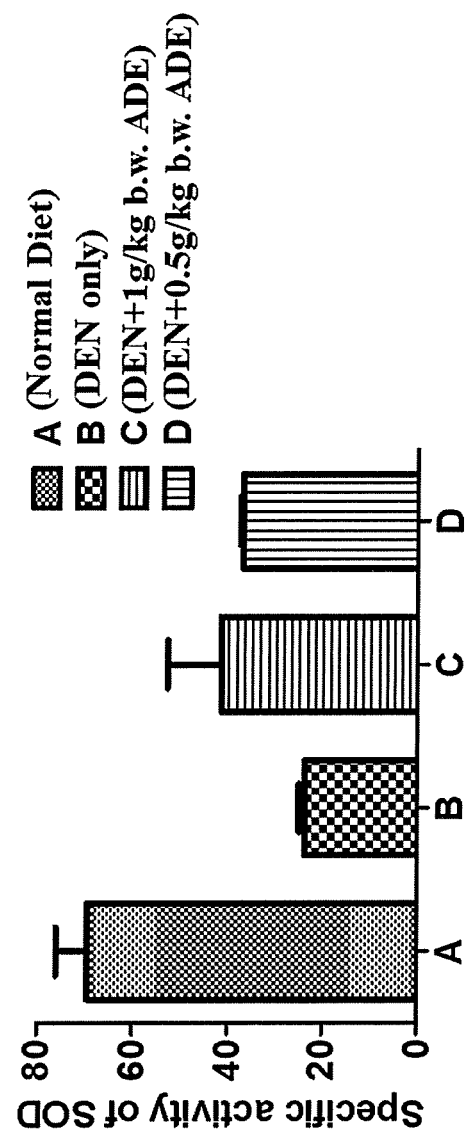
FIG. 8 is a graph showing the effect of ADE on serum superoxide dismutase (SOD) activity in male Wistar rats having DEN-induced liver cancer.

The role of G-CSF is in stimulation of bone marrow production of granulocytes and stem cells, while the MIP-1a is involved in chemotactic, pro-inflammatory, and homeostasis processes, and the GM-CSF is a glycoprotein that stimulates the attack on foreign cells. This in vitro example shows a dose-dependent effect of ADE on the expression of MIP-1a and GM-CSF in HepG2 cells after 48 h of contact, with no dose-dependent effect on the expression of G-CSF (FIG. 3). A multiplex panel in combination with Luminex assessment (Life Technologies, USA) was used to quantify the expression levels.

Example 5

Effect of ADE on Enzyme Levels of Female Rats having Breast Cancer

This is an in vivo experiment showing the improvement of Ajwa Date Extract (ADE) on the antioxidant system in rats having breast cancer induced by 7,12-Dimethylbenz[a]anthracene (DMBA).

The experiment of DMBA-induced breast cancer in female Wistar rats was comprised of six different treatment groups: the untreated controls (administered normal diet), DMBA-treated, DMBA-treated and orally administered 1 g/kg b.w. (body weight) of ADE, DMBA-treated and orally administered 0.5 g/kg b.w. of ADE, DMBA-treated and administered orally 2.5 mM melatonin, and DMBA-treated and administered 2.5 mM melatonin plus 1 g/kg b.w. of ADE. All six groups were treated daily for three months. On sacrification day, samples of blood were collected with the serum being separated and stored at −80° C.

The collected sera were analyzed for four mean activities namely, of superoxide dismutase (SOD) catalase, glutathione reductase (GR), and glutathione peroxidase (GPx). The means of the four activities in sera of the six treatment groups are illustrated in FIGS. 4-7. The mean serum SOD (FIG. 4), catalase (FIG. 5), GR (FIG. 6), and GPx (FIG. 7) in DMBA and ADE and/or melatonin administered rats was higher than that of the DMBA administered rats that were deprived of the ADE and/or melatonin.

Example 6

Effect of ADE on Enzyme Levels of Male Rats having Liver Cancer

Figure 9:
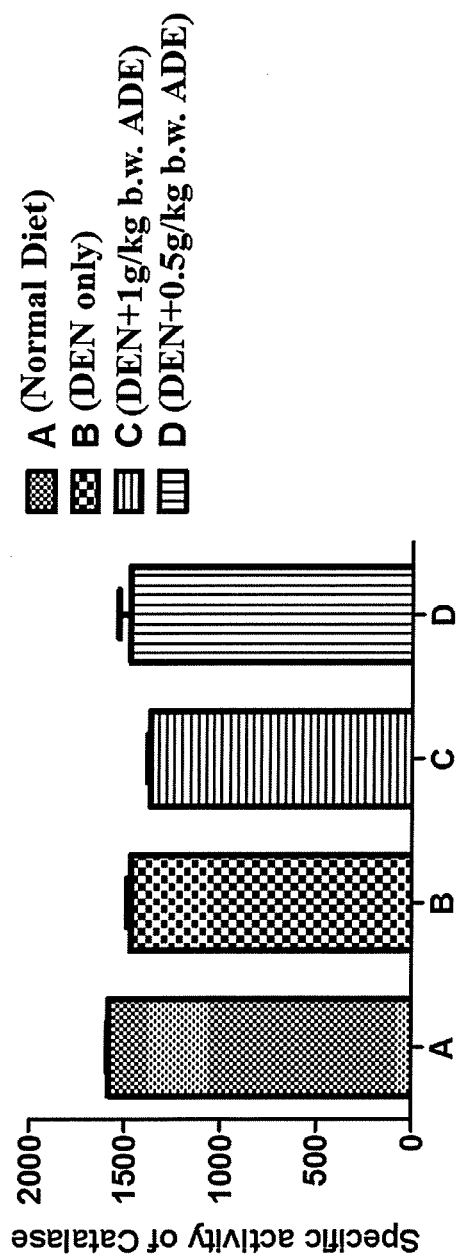
FIG. 9 is a graph showing the effect of ADE on serum catalase activity in male Wistar rats having DEN-induced liver cancer.
Figure 10:
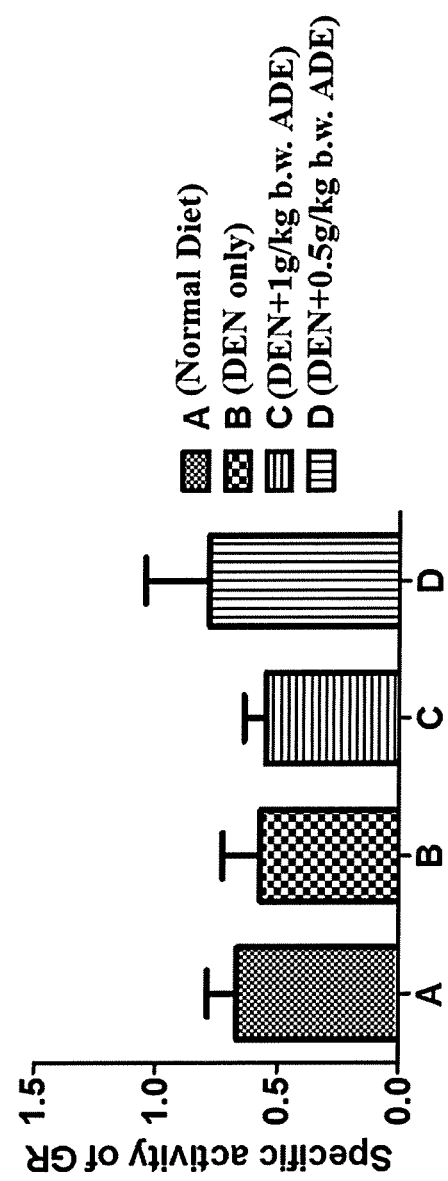
FIG. 10 is a graph showing the effect of ADE on glutathione reductase (GR) activity in male Wistar rats having DEN-induced liver cancer.
Figure 11:
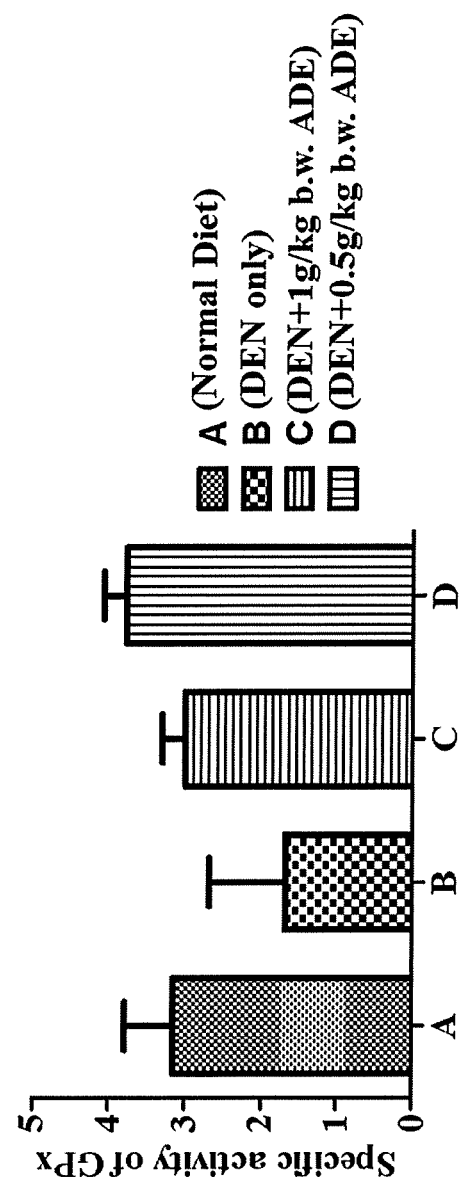
FIG. 11 is a graph showing the effect of ADE on glutathione peroxidase (GPx) activity in male Wistar rats having DEN-induced liver cancer.

This is an in vivo experiment showing the improvement of Ajwa Date Extract (ADE) on the antioxidant system in rats subjected to induction of liver cancer by diethyl nitrosoamine (DEN). The experimental design included four male Wistar rat groups: the untreated controls (administered normal diet), DEN-treated, DEN-treated and administered orally 1 g/kg b.w. (body weight) of ADE, and DEN-treated and administered orally 0.5 g/kg b.w. of ADE. All four rat groups were treated daily for three months. On scarification day, samples of blood were collected with their serum being separated and stored at −80° C. The collected sera were analyzed for four mean activities namely, of superoxide dismutase (SOD), catalase, glutathione reductase (GR), and glutathione peroxidase (GPx). The means of the four activities in sera of the four groups of rats are illustrated in FIGS. 8-11. There was an inverse relationship between the administered ADE concentrations and each of the mean serum levels of SOD (FIG. 8), GR (FIG. 10) and GPx (FIG. 11), in which the administration of lower concentration of ADE (0.5 g/kg b.w.) resulted in higher levels of these antioxidants compared to administration of the higher concentration of 1.0 g/kg b.w. The serum catalase activities of the rats were not affected by the administration of ADE (FIG. 9).

The invention claimed is:

1. A method for treating a breast cancer in a mammal comprising:
   measuring an initial activity of a catalase in a serum of the mammal,
   administering orally an extract of a *Phoenix dactylifera* fruit flesh to the mammal; and
   measuring an activity of the catalase in the serum of the mammal,
   wherein the extract is made by contacting a *Phoenix dactylifera* fruit flesh with methanol, where a weight ratio of the *Phoenix dactylifera* fruit flesh to the methanol is 1:1.5-1:3,
   wherein 0.1 to 1 g of the extract is administered per kg of the mammal per day, and
   wherein the activity of the catalase is increased 2%-50% after the administering compared to the initial activity of the catalase before the administering.

2. The method of claim 1, wherein the extract comprises at least one selected from the group consisting of p-coumaric acid, ferulic acid, sinapinic acid, a β-glucan, a flavonoid, and a polyphenol.

3. The method of claim 1, wherein the contacting is done for 12-96 h at 20-30° C.

4. The method of claim 1, wherein the *Phoenix dactylifera* fruit flesh is ground, blended, or cut.

5. The method of claim 1, wherein the extract is administered as a part of a composition, wherein the composition further comprises a food product, a pharmaceutically acceptable excipient, a pharmaceutically acceptable carrier, or an antioxidant.

6. The method of claim 5, wherein the composition is formed by reconstituting the extract into a liquid or gel, and wherein the extract is in the form of a dried powder before the reconstituting.

7. The method of claim 5, wherein the pharmaceutically acceptable carrier is present, and wherein the pharmaceutically acceptable carrier is an isotonic solution.

8. The method of claim 5, wherein the antioxidant is present, and wherein the antioxidant is at least one selected from the group consisting of melatonin, astaxamhin, tocotrienol, tocopherol, and lycopene.

9. The method of claim 1, wherein the administering is for a duration of 1-12 months.

10. The method of claim 1, wherein 0.3-0.7 g of the extract is administered per kg of the mammal per day, and wherein the activity of the catalase is increased 25%-44% after the administering compared to the initial activity of the catalase before the administering.

11. A method for treating a breast cancer in a mammal comprising:
    measuring an initial activity of a glutathione reductase in a serum of the mammal,
    administering orally a composition comprising melatonin and an extract of a *Phoenix dactylifera* fruit flesh to the mammal; and
    measuring an activity of the glutathione reductase in the serum of the mammal after the administering,
    wherein the extract is made by contacting a *Phoenix dactylifera* fruit flesh with methanol, where a weight ratio of the *Phoenix dactylifera* fruit flesh to the methanol is 1:1.5-1:3,
    wherein the composition is administered to provide 0.7 to 1 g of the extract per kg of the mammal per day,
    wherein a weight ratio of the melatonin to the extract is 1:65,000-1:1, and
    wherein the activity of the glutathione reductase is increased 110%-180% after the administering compared to the initial activity of the glutathione reductase before the administering.

12. The method of claim 11, wherein the weight ratio of the melatonin to the extract is 1:10,000-1:100.

13. The method of claim 11, wherein the administering is for a duration of 1-12 months.

14. The method of claim 11, wherein the extract comprises at least one selected from the group consisting of p-coumaric acid, ferulic acid, sinapinic acid, a β-glucan, a flavonoid, and a polyphenol.

15. The method of claim 11, wherein the contacting is done for 12-96 h at 20-30° C.

16. The method of claim 11, wherein the *Phoenix dactylifera* fruit flesh is ground, blended, or cut.

17. The method of claim 11, wherein the extract is administered as a part of a composition, wherein the composition further comprises a food product, a pharmaceutically acceptable excipient, or a pharmaceutically acceptable carrier, or an antioxidant.

18. The method of claim 17, wherein the composition is formed by reconstituting the extract into a liquid or gel, and wherein the extract is in the form of a dried powder before the reconstituting.

19. The method of claim 17, wherein the pharmaceutically acceptable carrier is present, and wherein the pharmaceutically acceptable carrier is an isotonic solution.

20. The method of claim 17, wherein the antioxidant is present, and wherein the antioxidant is at least one selected from the group consisting of astaxanthin, tocotrienol, tocopherol, and lycopene.

\* \* \* \* \*